US005559273A

United States Patent [19]

Guth et al.

[11] Patent Number: 5,559,273

[45] Date of Patent: Sep. 24, 1996

[54] AQUEOUS TEXTILE AUXILIARY COMPOSITIONS

[75] Inventors: Christian Guth, Birsfelden, Switzerland; Albert Stehlin, Rosenau, France; Christoph Kröhnke, Breisach-Oberrismsingen, Germany

[73] Assignee: Ciba-Geigy Corporation, Tarrytown, N.Y.

[21] Appl. No.: 484,374

[22] Filed: Jun. 7, 1995

Related U.S. Application Data

[63] Continuation of Ser. No. 107,768, filed as PCT/EP92/00299, Feb. 12, 1992 published as WO92/15664, Sep. 17, 1992, abandoned.

[30] Foreign Application Priority Data

Mar. 4, 1991 [CH] Switzerland .............................. 638/91

[51] Int. Cl.[6] .................................................. C07C 43/15

[52] U.S. Cl. ......................... 568/622; 252/8.81; 510/317; 510/302; 510/361

[58] Field of Search ............................... 252/174.23, 8.7, 252/8.9, 173, 174.21, 174.22; 525/406; 568/622

[56] References Cited

U.S. PATENT DOCUMENTS

| | | | |
|---|---|---|---|
| 3,737,387 | 6/1973 | Marple | 252/174.23 |
| 3,960,781 | 6/1976 | Freis | 252/541 |
| 4,115,457 | 9/1978 | Wiedemann | 252/351 |
| 4,363,699 | 12/1982 | De Ceuster | 162/71 |
| 4,539,353 | 9/1985 | Abel | 524/123 |
| 4,826,618 | 5/1989 | Borseth | 252/174 |
| 4,999,869 | 3/1991 | Holland et al. | 252/174.23 |
| 5,002,686 | 3/1991 | Guth | 252/174 |
| 5,013,327 | 5/1991 | Wahle | 8/125 |

FOREIGN PATENT DOCUMENTS

| | | |
|---|---|---|
| 0055818 | 7/1982 | European Pat. Off. . |
| 0114788 | 8/1984 | European Pat. Off. . |
| 0299691 | 1/1989 | European Pat. Off. . |
| 0308221 | 3/1989 | European Pat. Off. . |
| 0354344 | 2/1990 | European Pat. Off. . |
| 0360736 | 3/1990 | European Pat. Off. . |
| 2107169 | 5/1972 | France . |
| 2342365 | 9/1977 | France . |
| 1954080 | 5/1971 | Germany . |
| 1350275 | 4/1974 | United Kingdom . |
| 2075038 | 11/1981 | United Kingdom . |
| 2151252 | 7/1985 | United Kingdom . |

OTHER PUBLICATIONS

Conroy et al., Chem. Abs., 115:120698y (1991).

*Primary Examiner*—Richard L. Raymond
*Assistant Examiner*—Deborah Lambkin
*Attorney, Agent, or Firm*—Kevin T. Mansfield

[57] ABSTRACT

There is described a low-foaming, nonsilicone, aqueous textile auxiliary composition comprising (a) a homopolymer of an ethylenically unsaturated sulfonic or carboxylic acid or an anhydride thereof, (b) a nonionic surfactant of formula $$(1)\ R-O\!\left(\text{alkylene-O}\right)_p R_1,$$

wherein

R is an aliphatic radical of at least 8 carbon atoms, $R_1$ is hydrogen, $C_1$–$C_8$alkyl, a cycloaliphatic radical of at least 5 carbon atoms, styryl, an unsubstituted or halogen substituted $C_1$–$C_{10}$alkylisocyanato or an unsubstituted or by a hetero atom substituted cycloalkylisocyanato or cycloalkenylisocyanato radical, "alkylene" denotes an alkylene radical of 2 to 4 carbon atoms, and p is an integer from 2 to 60, and optionally (c) a hydrotropic agent.

The textile auxiliary composition is suitable for use as dispersants and for wetting, washing and/or bleaching fiber materials.

3 Claims, No Drawings

AQUEOUS TEXTILE AUXILIARY COMPOSITIONS

This application is a continuation of Ser. No. 08/107,768 filed Aug. 25, 1993 (now abandoned) which is a 35 U.S.C. 371 of PCT/EP92/00299 filed Feb. 12, 1992 published as WO92/15664, Sep. 17, 1992.

The present invention relates to a low-foaming, nonsilicone, aqueous textile auxiliary composition, to its preparation and to the versatile use as wetting agent, detergent, dispersant or as stabiliser in peroxide bleaching liquors.

The novel low-foaming, aqueous textile auxiliary composition comprises (a) a homopolymer of an ethylenically unsaturated sulfonic or carboxylic acid or an anhydride thereof, (b) a nonionic surfactant of formula (1) $R-O\leftarrow alkylene-O\rightarrow_p R_1$, wherein R is an aliphatic radical of at least 8 carbon atoms, $R_1$ is hydrogen, $C_1$–$C_8$alkyl, a cycloaliphatic radical of at least 5 carbon atoms, styryl, an unsubstituted or halogen substituted $C_1$–$C_{10}$alkylisocyanato or an unsubstituted or by a hetero atom substituted cycloalkylisocyanato or cycloalkenylisocyanato radical, "alkylene" denotes an alkylene radical of 2 to 4 carbon atoms, and p is an integer from 2 to 60, and optionally (c) a hydrotropic agent.

Because of its low-foaming properties the inventive textile auxiliary composition is free of silicon.

Ethylenically unsaturated monomeric sulfonic or carboxylic acids are suitable for preparing the homopolymers eligible for use as component (a). Monocarboxylic acids and dicarboxylic acids and anhyrides thereof as well as sulfonic acids may suitably be used, each of which acids contains an ethylenically unsaturated aliphatic radical and preferably not more than 7 carbon atoms. Monocarboxylic acids of 3 to 5 carbon atoms are preferred, typically acrylic acid, methacrylic acid, α-haloacrylic acid, 2-hydroxyethylacrylic acid, α-cyanoacrylic acid, crotonic acid and vinylacetic acid. Ethylenically unsaturated dicarboxylic acids are preferably fumaric acid, maleic acid or itaconic acid, and also mesaconic acid, citraconic acid, glutaconic acid and methylmalonic acid. The preferred anhydride of these acids is maleic anhydride.

Suitable monomeric sulfonic acids which can be used for the homopolymerisation of component (a) include vinylsulfonic acid or 2-acrylamido-2-methylpropanesulfonic acid. Preferred polymerised carboxylic acids are polymethacrylic acid and, more particularly, polyacrylic acid. The polyacrylic acids to be used in the practice of this invention have a molecular weight in the range from 4000 to 2 000 000, preferably from 4 500 to 800 000.

The homopolymers eligible for use as component (a) of the novel composition are prepared by methods which are known per se, conveniently by polymerising the appropriate monomer in the presence of a catalyst, suitably in the temperature range from 60° to 100° C.

The catalyst is preferably an initiator which forms free radicals. Illustrative examples of suitable initiators for carrying out the reaction are symmetrical aliphatic azo compounds such as azobisisobutyronitrile, azobis(2-methylvaleronitrile), 1,1'-azobis(1-cyclohexanitrile) and alkyl 2,2'-azobisisobutyrate, symmetrical diacyl peroxides, such as acetyl, propionyl or butyryl peroxide, benzoyl peroxide, bromine-, nitro-, methyl- or methoxy-substituted benzoyl peroxides as well as lauroyl peroxide; symmetrical peroxydicarbonates such as diethyl, diisopropyl, dicyclohexyl and dibenzyl peroxydicarbonate; tert-butyl peroctoate, tert-butyl perbenzoate or tert-butylphenyl peracetate as well as peroxycarbamates such as tert-butyl-N-(phenylperoxy)carbamate or tert-butyl-N-(2,3-dichloro- or-4-chlorophenylperoxy)-carbamate. Further suitable peroxides are: tert-butylhydroperoxide, di-tert-butylperoxide, cumene hydroperoxide, dicumene peroxide and tert-butyl perpivalate. A further suitable compound is potassium persulfate, which is preferably used in the practice of this invention.

The catalysts are normally used in amounts of 0.1 to 10 % by weight, preferably 0.5 to 2% by weight, based on the starting materials.

It is advantageous to carry out the polymerisation reaction in an inert atmosphere, conveniently in a nitrogen atmosphere.

The substituent R in formula (1) is conveniently the hydrocarbon radical of an unsaturated or saturated aliphatic monoalcohol of 8 to 22 carbon atoms. The hydrocarbon radical may be straight chain or branched. Preferably R is an alkyl or alkenyl radical of 9 to 14 carbon atoms.

The aliphatic saturated monoalcohols which may be suitably used are typically lauryl alcohol, myristyl alcohol, cetyl alcohol or stearyl alcohol, as well as synthetic alcohols such as 2-ethylhexanol, 1,1,3,3-tetramethylbutanol, octan-2-ol, isononyl alcohol, trimethylhexanol, trimethylnonyl alcohol, decanol, $C_9$–$C_{10}$alcohol, tridecyl alcohol, isotridecanol or linear primary alcohols (Alfols) of 8 to 18 carbon atoms. Some representatives of these Alfols are Alfol (8–10), Alfol (9–11), Alfol (10–14), Alfol (12–13) or Alfol (16–18). ("Alfol" is a registered trademark).

Illustrative examples of unsaturated monoalcohols are dodecenyl alcohol, hexadecenyl alcohol or oleyl alcohol.

$C_1$–$C_{10}$Alkyl denotes straight-chain or branched hydrocarbon radicals, typically methyl, ethyl, n-propyl, isopropyl, n-butyl, sec-butyl, tert-butyl, amyl, isoamyl or tert-amyl, heptyl, octyl, isooctyl, nonyl or decyl. Preferred radicals are those which contain 1 to 5, preferably 1 to 4, carbon atoms.

Cycloalkyl denotes cyclobutyl, cyclopentyl, cyclohexyl, cycloheptyl or cyclooctyl.

Examples of $C_1$–$C_{10}$Alkylisocyanato radicals are methylisocynato, ethylisocynato, 2-chlorethylisocyanato, n-propylisocynato, isopropylisocynato, n-butylisocynato, sec-butylisocynato, tert-butylisocynato, amylisocynato, isoamylisocynato, tert-amylisocynato, heptylisocynato, octylisocynato, isooctylisocynato, nonylisocynato or decylisocynato.

Examples for hetero atoms are oxygen, nitrogen or sulfur. Oxygen is preferred.

Cycloalkylisocyanoto radicals denote 4 to 8, preferably 5 to 7 carbon atoms. Examples for these radicals are cyclobutylisocynato, cyclopentylisocyanato, cyclohexylisocyanato, methylcyclohexylisocyanato, ethylcyclohexylisocyanato, hexylcycloisocyanato, cycloheptylisocyanato or cyclooctylisocyanato. Preferred cycloalkylisocyanoto radical is cyclohexylisocyanato.

The alcohol radicals may be single or in the form of mixtures of two or more components, such as mixtures of alkyl and/or alkenyl groups which are derived from soybean fatty acids, palm nut fatty acids or tallow oils.

$(Alkylene-O)_p$ chains are preferably of the ethylene glycol, ethylene propylene glycol or ethylene isopropylene glycol type; p is preferably 4 to 20.

The polyadducts of unsaturated or saturated aliphatic monoalcohols and ethylene oxide may be further reacted with $C_1$–$C_{10}$alkylisocyanates to give end-capped nonionic surfactants.

Illustrative examples of nonionic surfactants are:

polyadducts of preferably 2 to 60 mol of alkylene oxides, preferably ethylene oxide, individual ethylene oxide units of which polyadducts can be replaced by substituted epoxides, such as buten-1-oxide or butene-2-oxide and/or propylene oxide, with higher unsaturated or saturated fatty alcohols of 8 to 22 carbon atoms.

The reaction products of the polyadducts of preferably 2 to 60 mol of alkylene oxides, preferably ethylene oxide, and higher unsaturated or saturated $C_8$–$C_{22}$fatty alcohols with $C_1$–$C_{10}$alkylisocyanates.

Interesting nonionic surfactants suitable as component (a) have the formula $$R-O+CH_2-CH_2-O\frac{}{}_{n_1}+\underset{Y_1}{\underset{|}{CH}}-\underset{Y_2}{\underset{|}{CH}}-O\frac{}{}_{m_1}R_1, \qquad (2)$$

wherein one of $Y_1$ and $Y_2$ is methyl or ethyl and the other is hydrogen, $n_1$ is an integer from 2 to 40, $m_1$ is an integer from 0 to 15, and R and $R_1$ are as defined for formual (1).

Especially interesting nonionic surfactants are those of formula $$R_2-O+CH_2-CH_2-O\frac{}{}_{n_2}+\underset{Y_3}{\underset{|}{CH}}-\underset{Y_4}{\underset{|}{CH}}-O\frac{}{}_{m_2}R_3, \qquad (3)$$

wherein $R_2$ is $C_9$–$C_{14}$alkyl, $R_3$ is hydrogen, $C_1$–$C_4$alkyl, a cycloaliphatic radical of at least 6 carbon atoms or a $C_1$–$C_{10}$alkylisocyanato radical, one of $Y_3$ and $Y_4$ is methyl and the other is hydrogen, $m_2$ is an integer from 0 to 8, and $n_2$ is an integer from 4 to 10.

Important nonionic surfactants are those of formula $$R-O+\text{alkylene-O}\frac{}{}_{p}R_4, \qquad (4)$$

wherein

R is an aliphatic radical of at least 8 carbon atoms, $R_4$ is an unsubstituted or halogen substituted $C_1$–$C_{10}$alkylisocyanato or an unsubstituted or by a hetero atom substituted cycloalkylisocyanato or cycloalkenylisocyanato radical, "alkylene" denotes an alkylene radical of 2 to 4 carbon atoms, and p is an integer from 2 to 60.

Among these nonionic surfactants, those compounds are especially preferred in which the $C_1$–$C_{10}$alkylisocyanato radical is n-butylisocyanato or isopropylisocyanato.

Further important nonionic surfactants are those of formula $$R_2-O+CH_2-CH_2-O\frac{}{}_{n_3}+\underset{Y_5}{\underset{|}{CH}}-\underset{Y_6}{\underset{|}{CH}}-O\frac{}{}_{m_3}R_5, \qquad (5)$$

wherein $R_2$ is $C_9$–$C_{14}$alkyl, $R_5$ is hydrogen or butyl, one of $Y_5$ and $Y_6$ is methyl and the other is hydrogen, $m_3$ is an integer from 0 to 3, and $n_3$ is an integer from 4 to 8.

The nonionic surfactants of formula (4) are novel compounds. These compounds constitute a further object of the present invention.

The preparation of the end capped surfactants of formulae (1) to (5) is carded out in a manner which is known per se, conveniently by reacting the corresponding alkylene oxide polyadducts with thionyl chloride and subsequently reacting the resultant chlorinated compound with an alcohol of the formula $R_1$—OH, wherein $R_1$ is alkyl or cycloalkyl.

If a compound of formula (4) is used as component (b), the known per se alkyl polyalkylene glycol ethers are reacted with $C_1$–$C_{10}$alkylisocyanate using a catalyst or a mixture of catalysts according to the following reaction scheme:

$$R-O+\text{Alkylen-O}\frac{}{}_{p}H + RNCO \longrightarrow R-O+\text{Alkylen-O}\frac{}{}_{p}R_4$$

wherein R, $R_4$ and p have the above defined meaning.

A mixture of nonionic surfactants may also be used as the nonionic surfactant (b).

The following compounds may suitably be used as optional component (c) of the composition of the invention:

alkali metal salts and amine salts of $C_1$–$C_{10}$alkylphosphoric acid esters;

diols, such as hexylene glycol;

sulfonates of terpenoids or mono- or binuclear aromatic compounds, for example the sulfonates of camphor, toluene, xylene, cumene and naphthol;

alkali metal salts and amine salts of saturated or unsaturated $C_3$–$C_{12}$di- or polycarboxylic acids, for example of malonic, succinic, glutaric, adipic, pimelic, suberic, azelaic and sebacic acid, of undecanedicarboxylic and dodecanedicarboxylic acid, of fumaric, maleic, tartaric and malic acid as well as citric and aconitic acid.

2-Ethylhexyl sulfate is especially preferred.

It is preferred to use a textile auxiliary composition in which component (a) is polyacrylic acid, component (b) is a nonionic surfactant of formula ( 1 ) or a mixture of nonionic surfactants of formulae (1) to (5), and optional component (c) is 2-ethylhexyl sulfate.

A particularly interesting textile auxiliary composition is one wherein component (a) is polyacrylic acid and component (b) is a nonionic surfactant of formula (3), wherein $R_3$ is a $C_1$–$C_{10}$alkylisocyanato radical and $m_2$=0.

The textile auxiliary composition of this invention can be prepared by simple stirring of components (a), (b) and optionally (c).

The composition is preferably prepared by mixing components (a), (b) and optionally (c), with stirring, and adding deionised water until a homogeneous solution is obtained.

The textile auxiliary composition of this invention has a pH in the range from 3 to 5, preferably from 3.5 to 4.5.

Preferred textile auxiliary composition of the invention conveniently comprises, based on the entire composition:

2 to 22% by weight, preferably 5 to 18% by weight, of component (a), 10 to 95% by weight, preferably 25 to 60% by weight, of component (b), 0 to 15% by weight, preferably 1 to 10% by weight, of component (c), and and water to make up 100% by weight.

The novel formulations is a low-foaming and nonsilicone textile auxiliary having soil dissolving properties. Owing to its liquid form, it is easy to handle and therefore especially suitable for modem metering devices. It has a multipurpose utility and is consequently suitable for different end use requirements.

It may be used as wetting agent, textile detergent, dispersant or stabiliser in peroxide bleaching liquors.

Furthermore it is suitable as household washing agent.

Accordingly, the invention relates to a process for wetting, washing and/or bleaching fiber materials, which comprises treating said materials, in aqueous medium, in the presence of a textile auxiliary composition in which component (a) is a homopolymer of an ethylenically unsaturated sulfonic or carboxylic acid or an anhydride thereof, component (b) is a nonionic surfactant of formula $$(1)\ R-O\left(\text{alkylene-O}\right)_{p}R_1,$$

wherein

R is an aliphatic radical of at least 8 carbon atoms, $R_1$ is hydrogen, $C_1$–$C_8$alkyl, a cycloaliphatic radical of at least 5 carbon atoms, styryl, an unsubstituted or halogen substituted $C_1$–$C_{10}$alkylisocyanato or an unsubstituted or by a hetero atom substituted cycloalkylisocyanato or cycloalkenylisocyanato radical, "alkylene" denotes an alkylene radical of 2 to 4 carbon atoms, and p is an integer from 2 to 60, and optionally (c) is a hydrotropic agent.

For this process it is preferred to use a textile auxiliary composition in which component (a) is a polyacrylic acid, component (b) is a nonionic surfactant of formula (3), wherein $R_3$ is n-butyl or a $C_1$–$C_{10}$alkylisocyanato radical, and $m_2$=0, and component (c) is a hydrotropic agent.

The amounts in which the textile auxiliary composition of the invention is added to the treatment liquors are from 0.1 to 60 g/liter, preferably from 0.2 to 10 g/liter, of treatment liquor. These liquors may contain further ingredients, such as desizing agents, dyes, fluorescent whitening agents, synthetic resins and alkalies such as sodium hydroxide, hydrogen peroxide and magnesium salts.

Suitable fiber materials are: cellulose, especially non-pretreated natural cellulose such as hemp, linen, jute, viscose staple, viscose, acetate rayon, natural cellulose fibres and, preferably, raw cotton, wool, polyamide, polyacrylonitrile or polyester fabrics and blends, for example polyacrylonitrile/cotton or polyester/cotton blends.

The fiber material can be in any form of presentation, for example the cellulosic material may be in the form of loose stock, yam, woven or knitted goods. The material is thus usually always in the form of textile materials which are made from pure cellulosic textile fibres or from blends of cellulosic textile fibres with synthetic textile fibres. The fibre material can be treated continuously or batchwise in aqueous liquor.

The aqueous treatment liquors can be applied to the fibre materials in known manner, conveniently by impregnation on the pad to a pick-up of ca. 70–120% by weight. The pad method is used especially in the pad-steam and pad-batch process.

Impregnation can be effected in the temperature range from 10° to 60° C., but preferably at room temperature. After impregnation and expression, the cellulosic material is subjected to an optional heat treatment in the temperature range from 80° to 140° C. The heat treatment is preferably carded out by steaming at 95°–140° C., preferably 100°–106° C. Depending on the nature of the heat development and the temperature range, the heat treatment can take from 30 seconds to 60 minutes. In the pad-batch process, the impregnated goods are rolled up without being dried, packed in a plastic sheet, and stored at room temperature for 1 hour to 24 hours.

The treatment of the fibre materials can also be carried out in long liquors at a liquor to goods ratio of typically 1:3 to 1:100, preferably 1:4 to 1:25, and at 10° to 100° C., preferably 60° to 98° C., for ca. ¼ to 3 hours under normal conditions, i.e. under atmospheric pressure, in conventional apparatus such as a jigger, jet or a winchbeck. If desired, the heat treatment can also be carded out in the temperature range up to 150° C., preferably from 105° to 140° C., under pressure in HT (high-temperature) apparatus.

If the process makes it necessary, the fibre materials are subsequently thoroughly rinsed with hot water of 90°–98° C. and then with warm and, finally, cold water, if appropriate neutralised, and then dried at elevated temperature.

In the following illustrative Examples percentages are always by weight.

Preparation of the nonionic surfactants which are end-capped with an isocyanato radical and suitable for use as component (b)

Example 1: 51 g (c. 0.1 mol) of the polyadduct of 1 mol of decyl alcohol and 8 mol of ethylene oxide are dissolved in 25 ml of dry tetrahydrofuran and to the solution are added 8.9 g (0.105 mol) of isopropyl isocyanate. After addition of a catalyst mixture consisting of 100 µl each of dibutyltin laurate and triethylamine, the reaction mixture is heated, with stirring, to 60° C. under a stream of inert gas. The reaction is terminated after 90 minutes by pouring the reaction mixture into petroleum ether and isolating the almost colourless precipitate. The precipitate is dried at 50° C. under vacuum to give 56.8 g of slightly oily product.

Example 2: 153 g (c. 0.3 mol) of the polyadduct of 1 mol of decyl alcohol and 8 mol of ethylene oxide are charged, without solvent, to a reactor in an inert gas atmosphere and 30.9 g (0.105 mol) of n-butyl isocyanate are added dropwise, with stirring. After addition of a catalyst mixture consisting of 100 µl each of dibutyltin laurate and ttiethylamine, slight warming of the reaction mixture to c. 40° C. ensues initially. The reaction is fully complete after 60 minutes at a temperature of 60° C. Finally, the reaction mixture is poured into 100 ml of petroleum ether (40–80). The precipitated liquid product is isolated and dried at 50° C. under vacuum. Yield: 167 g.

Example 3: 18.4 g (0.036 mol) of the polyadduct of 1 mol of decyl alcohol and 8 mol of ethylene oxide are dissolved in 25 ml of dry tetrahydrofuran. Then 4.8 g (0.038 mol) of tetrahydropyran-2-yl isocyanate are added dropwise in an inert gas atmosphere. To the well stirred batch is finally added a catalyst mixture consisting of 50 µl each of dibutyltin laurate and triethylamine. The reaction is fully complete after c. 100 minutes at a reaction temperature of 60° C. The batch is poured into 100 ml of petroleum ether, whereupon the highly viscous, milky-white product precipitates and is subsequently dried under vacuum. Yield: 23.6 g.

Example 4: 18.4 g (0.036 mol) of the polyadduct of 1 mol of decyl alcohol and 8 mol of ethylene oxide are dissolved in 25 ml of dry tetrahydrofuran. After addition of a catalyst mixture consisting of 100 µl each of dibutyltin laurate and triethylamine in an inert gas atmosphere, slight warming of the reaction mixture to c. 40° C. ensues initially. Then 4.8 g (0.038 mol) of cyclohexylisocyanate are added dropwise. The reaction is fully complete after c. 200 minutes at a reaction temperature of 60° C. The batch is poured into 120 ml of petroleum ether, whereupon the lower, liquid phase of the colourless product is separated and subsequently dried under vacuum. Yield: 21.5 g.

Example 5: 12.5 g (0.021 mol) of the polyadduct of 1 mol of decyl alcohol and 11 mol of ethylene oxide are dissolved in 25 ml of dry tetrahydrofuran. Then 2.4 g (0.023 mol) of 2-chlorethyl isocynate and a catalyst mixture consisting of 50 µl each of dibutyltin laurate and triethylamine are added. After areaction time of 20 hpurs at 60° C. the product is isolated removing the volatile parts of the solution in high vaccum at 50° C. Yield: 14.4 g.

Preparation of the formulations

Example 6:

| | |
|---|---|
| 340 g | of a 25% polyacrylic acid having a molecular weight of 190 000 are added to |
| 247 g | of deionised water. |

The pH is adjusted to 3.0 with

| | |
|---|---|
| 8 g | of 30% sodium hydroxide solution. Then, with stirring, |
| 70 g | of a 40% solution of the sodium salt of 2-ethylhexyl sulfate, |
| 250 g | of the nonionic surfactant of formula $R-O-(CH_2CH_2O)_{\overline{8}}R_1$, wherein R is a $C_{9/11}$alkyl radical and $R_1$ is butyl, |
| 34 g | of the polyadduct of 1 mol of a $C_{13}$oxoalcohol and 9 mol of ethylene oxide, and |
| 51 g | of the polyadduct of 1 mol of a $C_{13}$oxoalcohol and 10 mol of ethylene oxide |

are added in succession.

The slightly viscous formulation so obtained has a pH of 3 and a cloud point of c. 67° C.

Example 7:

| | |
|---|---|
| 340 g | of a 25% polyacrylic acid having a molecular weight of 243 000 are added to |
| 247 g | of deionised water. |

The pH is adjusted to 3.0 with

| | |
|---|---|
| 8 g | of 30% sodium hydroxide solution. Then, with stirring, |
| 70 g | of a 40% solution of the sodium salt of 2-ethylhexyl sulfate, |
| 250 g | of the polyadduct of 1 mol of decyl alcohol and 5 mol of ethylene oxide/8 mol of propylene oxide, and |
| 95 g | of the polyadduct of 1 mol of tridecyl alcohol and 9.75 mol of ethylene oxide |

are added in succession.

The slightly viscous formulation so obtained has a pH of 3.5 and a cloud point of c. 46° C.

Example 8:

| | |
|---|---|
| 340 g | of a 25% polyacrylic acid having a molecular weight of 190 000 are added to |
| 247 g | of deionised water. |

The pH is adjusted to 3.0 with

| | |
|---|---|
| 8 g | of 30% sodium hydroxide solution. Then, with stirring, |
| 70 g | of a 40% solution of the sodium salt of 2-ethylhexyl sulfate, |
| 250 g | of the polyadduct of 1 mol of decyl alcohol and 8 mol of ethylene oxide and 1 mol of n-butyl isocyanate, |
| 34 g | of the polyadduct of 1 mol of a $C_{13}$oxoalcohol and 9 mol of ethylene oxide, and |
| 51 g | of the polyadduct of 1 mol of a $C_{13}$oxoalcohol and 10 mol of ethylene oxide |

are added in succession.

The slightly viscous formulation so obtained has a pH of 4.1 and a cloud point of c. 58° C.

Application Examples

Example 9: The formulations prepared in Examples 4–6 are tested for their detergent properties. This is done by washing a polyester/cotton blend, which has been artificially soiled with soot and engine oil, in an Ahiba dyeing machine with twist for 30 minutes at 40° C. and at a liquor to goods ratio of 1:25. The amount of active substance is 1 g/l and the pH of the wash liquor is adjusted to 10 with NaOH. At the end of the washing procedure, the fabric is rinsed, hydroextracted and dried.

The detergent properties are determined by measuring the difference in colour between the washed and an unwashed sample. The higher the reflectance, the better the detergent effect. The differences measured are reported in Table 1 (2).

The formulations are foamed in accordance with DIN 53 902, the measurements being made at room temperature using 200 ml of a wash liquor containing 1 g of active substance/l of the formulations of Examples 4, 5 and 6 [Table 1 (3)].

Example 10: Raw cotton tricot fabric is treated for 30 minutes at 90° C. in a bleach bath which contains the following ingredients:

2 g/l of the formulations prepared according to Examples 4–6

1 g/l of NaOH (100%), and 5 ml/l of $H_2O_2$ (35%).

After bleaching, the fabric is washed off hot and cold, neutralised and dried.

The addition of the novel formulations results in a substrate of good absorbency being obtained after the bleach.

The whiteness level is increased from −77 to 56 CIBA-GEIGY whiteness units [Table 1(4)].

The wetting properties of the individual formulations is determined in accordance with DIN 53 901 [g/l for 25" wetting time (=WT)]. The results are reported in Table 1 (1).

TABLE 1

| Test criteria | Formulation of Example 4 | Formulation of Example 5 | Formulation of Example 6 |
|---|---|---|---|
| (1) wetting power (g/l for 25" WT) | 1.3 | 1.1 | 1.4 |
| (2) detergent effect colour diff.abs.: | 21.7 | 21.2 | 18.2 |
| (3) foam height [ml] (immed./after 1') | 50/50 | 90/80 | 80/70 |
| (4) whiteness | 56 | 56 | 56 |

Example 11: The formulations prepared in Examples 6 to 8 are stable for use in highly concentrated alkaline stock liquors containing up to 360 g/l of NaOH.

Example 12: A cotton/polyester blend (33:67) is printed on shade with a printing paste comprising 20 g/kg of the dye of the formula (I)

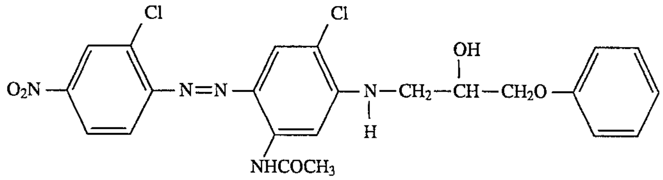

12 g/kg of the dye of the formula (II)

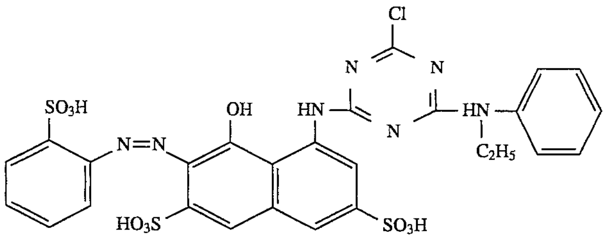

5 g/kg of the dye of the formula (III)

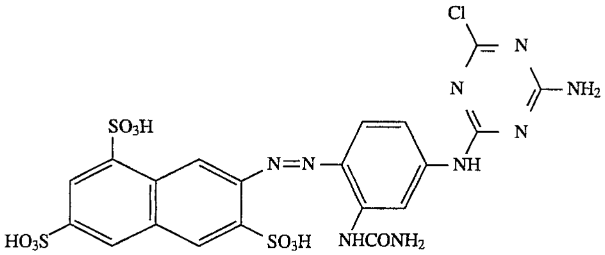

as well as 963 g/kg of a stock thickener comprising

| | |
|---|---|
| 40 parts | of Permutit $H_2O$ |
| 4 parts | of an ethyoxylated fatty acid derivative |
| 200 parts | of an hydrocarbon compound, for example ® Sangajol |
| 400 parts | of sodium alginate 6% |
| 50 parts | of urea |
| 15 parts | of $NaHCO_3$ |
| 291 parts | of Permutit water, |

dried for 5 minutes at 90° C., and afterwards fixed in a fixation unit for 8 minutes at 180° C. with superheated steam.

The printed material is given a wash-off in an AHIBA machine. For this purpose, two wash baths A and B are prepared with Permutit water. Wash bath A contains 3 g/l, based on 100% of the goods, of the detergent formulation of Example 6. Wash bath B contains no further ingredients. The liquor ratio is 1:30. Three uniformly printed samples on a white ground are each washed in succession in the same bath for 5 minutes at 90° C. The samples are then rinsed 3 times within 2 minutes cold in Permutit water. After drying the material at 90° to 100° C., a print is obtained wherein the white fond is less soiled compared to aprint which was not washed with the formulation according to the invention.

Example 13: The procedure of Example 12 is repeated, but using the formulation prepared in Example 6 for the wash-off.

What is claimed is:

1. A low foaming, nonsilicone, aqueous textile auxiliary composition, consisting essentially of (a) 2 to 22% by weight of a polyacrylic acid, ($b_1$) 25 to 60% of a nonionic surfactant of the formula (1) $R-O-(alkylene-O)_p-H$ and a nonionic surfactant of the formula (3) $R_2-O-(CH_2-CH_2-O)_{n_2}-(CH(Y_3)-CH(Y_4)-O)_{m_2}-R_3$ or ($b_2$) 25 to 60% of a nonionic surfactant of the formula (3), wherein R is an aliphatic radical of 8 to 22 carbon atoms.

$R_2$ is $C_9$–$C_{14}$alkyl, $R_3$ is $C_1$–$C_4$alkyl, $Y_3$ and $Y_4$ are hydrogen, $m_2$ is an integer from 0 to 8

$n_2$ is an integer from 4 to 10, p is an integer from 4 and 20 and optionally (c) 0 to 15% by weight of 2-ethylhexyl sulfate.

2. A textile auxiliary composition according to claim 1, wherein $R_3$ is butyl.

3. A textile auxiliary composition according to claim 1, which has a pH in the range from 3 to 5.

* * * * *